United States Patent [19]

Zahir

[11] Patent Number: 4,954,580
[45] Date of Patent: Sep. 4, 1990

[54] EPOXYSILOXANES

[75] Inventor: Sheik A. Zahir, Oberwil, Switzerland

[73] Assignee: Ciba-Geigy Corporation, Ardsley, N.Y.

[21] Appl. No.: 273,525

[22] Filed: Nov. 21, 1988

[51] Int. Cl.$^5$ .................... C08G 77/04; C07D 303/02
[52] U.S. Cl. .................... 525/476; 525/479; 525/481; 525/525; 528/27; 528/31; 522/148; 549/215
[58] Field of Search .................... 528/27, 31; 549/215; 525/479, 476, 481, 525; 522/148

[56] References Cited

U.S. PATENT DOCUMENTS

| | | | |
|---|---|---|---|
| 2,883,397 | 4/1959 | Bailey | 528/27 |
| 3,455,877 | 7/1969 | Plueddemann | 528/25 |
| 4,208,503 | 6/1980 | Martin | 528/14 |
| 4,395,527 | 7/1983 | Berger | 528/26 |

FOREIGN PATENT DOCUMENTS

| | | |
|---|---|---|
| 0218228 | 4/1987 | European Pat. Off. |
| 1768785 | 5/1974 | Fed. Rep. of Germany |
| 61-133222 | 6/1986 | Japan |
| 834326 | 5/1960 | United Kingdom |

OTHER PUBLICATIONS

Lee & Neville, "Handbook of Epoxy Resins", McGraw Hill, New York 1982, pp. 15–13.
E. P. Plueddemann, J. Chem. Eng. Data, 5, 59 (1960).
E. P. Pleuddemann et al., J. Am. Chem. Soc., 81, 2632 (1959).

Primary Examiner—John C. Bleutge
Assistant Examiner—Ralph Dean, Jr.
Attorney, Agent, or Firm—Luther A. R. Hall

[57] ABSTRACT

Epoxysiloxanes having, per molecule, at least two groupings of the formula

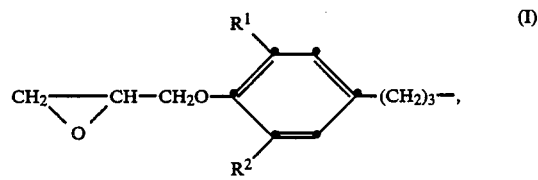

in which $R^1$ and $R^2$ independently of one another are $C_1$-$C_{10}$alkyl, $C_1$-$C_{10}$alkyoxy, $C_3$-$C_8$cycloalkyl, $C_6$-$C_{10}$aryl, benzyl or a halogen atom and in which each grouping of the formula I in each case is attached directly to a silicon atom of the siloxane radical, are suitable for use as epoxy resins. They can be used together with customary epoxy resin curing agents, for example, for the production of adhesives, sealing materials, lacquers or encapsulating resins, and afford products having excellent properties. The epoxysiloxanes according to the invention are also valuable reactive thinners and flexibilizers for curable epoxy resin mixtures.

15 Claims, No Drawings

EPOXYSILOXANES

The invention relates to epoxysiloxanes having at least two 3-(4-glycidyloxyphenyl)-propyl groupings disubstituted in the 3- and 5-position of the benzene ring per molecule, a process for their preparation and their use as epoxy resins.

Epoxysiloxanes of various structures are known.

In Lee and Neville's "Handbook of Epoxy Resins", pages 15–13, McGraw Hill, New York, 1982, 1,3-bis-(glycidyloxypropyl)-tetramethyldisiloxane and its use as an epoxy resin are described. The preparation of this compound by reacting allyl glycidyl ether with tetramethyldisiloxane is disclosed, for example, in U.S. Pat. No. 3,455,877. Longer chain siloxanes containing glycidyloxypropyl end groups or having glycidyloxypropyl side groups in the polysiloxane main chain are known from GB No. 834,326 or from German Auslegeschrift No. 1,768,785. In J. Chem. Eng. Data 5, 59–62 (1960), E. P. Plueddemann discusses the use of these compounds as casting resins.

In J. Am. Chem. Soc. 81, 2632–2635 (1959), E. P. Plueddemann and G. Fenger describe the preparation of a multiplicity of epoxy silicon compounds in which the group containing an epoxy function is in each case attached directly to silicon via a carbon silicon bond. Inter alia, 1,3-bis-(2-glycidyloxyphenylpropyl)-tetramethyldisiloxane is also mentioned.

U.S. Pat. No. 4,395,527 describes siloxane containing polymers, in particular polyimides. These polymers can have a multiplicity of functional groups, including epoxy groups. In Example 64 a siloxane containing epoxy groups, 1,3-bis-[4-(2,3-epoxypropyl)-phenoxybutyl]-tetramethyldisiloxane, and its use as an epoxy resin are also described.

Japanese Preliminary Published Application No. 86/133,222 describes epoxy resin compositions of matter containing a phenol modified polysiloxane which is obtained by reacting a phenolic resin with a polysiloxane having epoxy groups and other reactive functional groups.

In EP-A No. 218,228 epoxy resin compositions of matter are disclosed which contain siloxane copolymers. The siloxane compounds are prepared by reacting epoxy resins containing alkenyl groups with polysiloxanes, reaction products of alkenyl containing phenolic resins with epichlorohydrin or products of an incomplete reaction of 2-allylphenol with known epoxy resins being mentioned as epoxy resins containing alkenyl groups. Allyl-containing epoxyphenol and epoxycresol novolaks are disclosed as examples of such epoxy resins.

The present invention relates to novel epoxysiloxanes having, per molecule, at least two groupings of the formula I

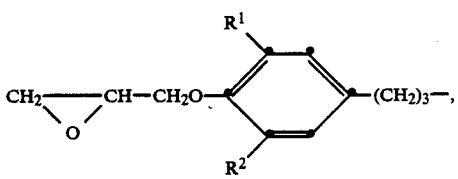

in which $R^1$ and $R^2$ independently of one another are $C_1$–$C_{10}$alkyyl, $C_1$–$C_{10}$alkoxy, $C_3$–$C_8$cycloalkyl, $C_6$–$C_{10}$aryl, benzyl or a halogen atom and in which each grouping of the formula I in each case is attached directly to a silicon atom of the siloxane radical.

The compounds according to the invention can be prepared by hydrosilylation of a 4-allylphenyl glycidyl ether of the formula II

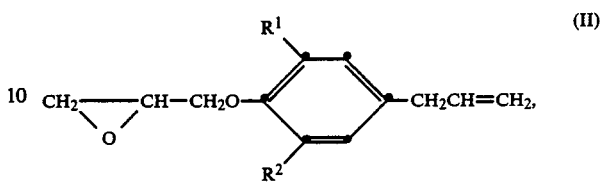

in which $R^1$ and $R^2$ are as defined above, with a siloxane containing at least two H—Si≡ groups, in the presence of a catalyst.

The hydrosilylation, i.e. the addition of compounds with one or more Si—H bonds to olefinic double bonds is known and is described, for example, by J. L. Speier et al. in J. Am. Chem. Soc. 79, 974–979 (1957) or by R. N. Meals in Pure and Appl. Chem. 13, 141–57 (1966). Suitable catalysts are, for example, compounds of transition metals, in particular of platinum, for example chloroplatinic acid. A multiplicity of catalysed hydrosilylations of this type is described in J. L. Speier, Advances in Organometallic Chemistry 17, 407–447 (1979).

The starting materials of the formula II are known or can be prepared by methods which are known per se by reacting the corresponding 2,6-disubstituted 4-allylphenols with epihalogenohydrins, especially epichlorohydrin, in the presence of catalysts. A suitable process for the preparation of such compounds is described, for example, in Example A of EP-A No. 205,402.

The radicals $R^1$ or $R^2$ in the groupings of the formula I can be different or, preferably, identical.

Alkyl and alkoxy substituents $R^1$ and $R^2$ can be linear or branched. Examples of such groups are: methyl, ethyl, n-propyl, isopropyl, n-butyl, sec-butyl, tert-butyl, pentyl, hexyl, heptyl, octyl, nonyl, decyl and the alkoxy groups corresponding to these alkyl groups. Cycloalkyl $R^1$ and/or $R^2$ is, for example, cyclopropyl, cyclobutyl, cyclopentyl, cyclohexyl, cycloheptyl or cyclooctyl. Suitable aryl groups $R^1$ and/or $R^2$ are, for example, 1-naphthyl, 2-naphthyl and, in particular, phenyl. Examples of halogen atoms $R^1$ and/or $R^2$ are fluorine, chlorine, iodine and, in particular, bromine atoms.

Compounds in which $R^1$ and $R^2$ independently of one another are $C_1$–$C_5$alkyl, $C_1$–$C_5$alkoxy, $C_5$–$C_6$cycloalkyl, phenyl, benzyl or a chlorine or bromine atom are preferred. Compounds in which $R^1$ and/or $R^2$ are ethyl, isopropyl, tertbutyl, cyclohexyl, phenyl, a bromine atom and, in particular, methyl are particularly preferred.

In the hydrosilylation of the 2,6-disubstituted 4-allylphenyl glycidyl ethers of the formula II, in principle, any desired siloxane can be used which contains at least two H—Si≡ groups, i.e. any polysiloxane compound having at least two organosiloxane units having terminal and/or lateral Si—H groups. A large number of such hydrogen siloxanes are known and some are commercially available. These can be linear, branched or cyclic disiloxanes, oligosiloxanes or polysiloxanes. The molecular weight of the hydrogen-siloxanes can vary within a wide range, for example from about 135 to about 60,000, preferably from about 135 to about 5,000 and particularly up to about 2,500. The synthesis of the epoxysiloxanes according to the invention is effected, for example, in accordance with scheme 1 below

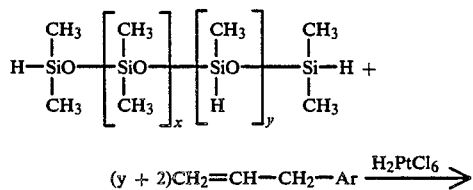

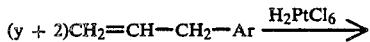

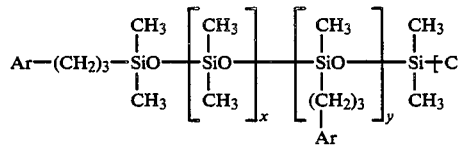

Ar in scheme (1) being 3,5-disubstituted 4-glycidyloxyphenyl. All or only some of the Si—H groups of the hydrogen-siloxanes can be reacted with the 4-allylphenyl glycidyl ether of the formula II, as desired and according to the end use, and the residual Si—H groups can, if desired, be reacted with other compounds containing olefinic double bonds, for example acrylate esters or acrylonitrile.

Examples of suitable epoxy siloxanes according to the invention are compounds of the formulae III to V

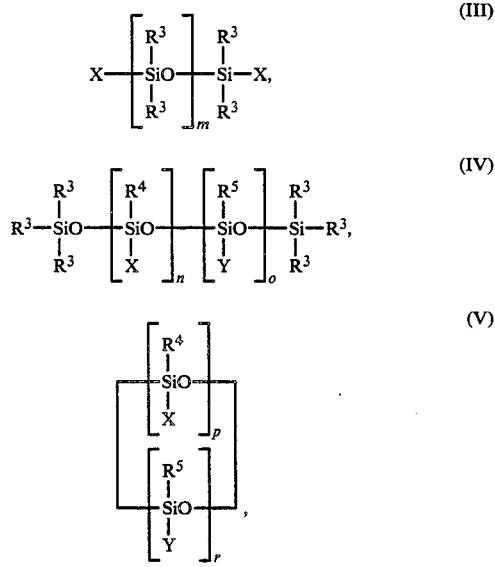

in which $R^3$ to $R^5$ independently of one another are $C_1$–$C_5$alkyl, $C_1$–$C_5$fluoroalkyl or phenyl, X is a grouping of the formula I, Y is one of the radicals $R^3$ to $R^5$ or is a group —$(CH_2)_2$—CN or —$(CH_2)_2$—$COOR^6$ in which $R^6$ is $C^1$–$C^5$alkyl, m is an integer from 1 to 500, n is an integer from 2 to 500, o is zero or an integer from 1 to 500, p is an integer from 2 to 10, r is zero or an integer from 1 to 8 and p+r is at least 3.

The alkyl and/or fluoroalkyl substituents $R^3$ to $R^5$ and $R^6$ are preferably linear. The following are examples of groups of this type: methyl, ethyl, propyl, butyl, pentyl, trifluoromethyl, 3,3,3-trifluoropropyl, 2,2,2-trifluoroethyl.

Epoxysiloxanes of the formulae III, IV or V in which $R^3$ to $R^5$ independently of one another are methyl, ethyl, 3,3,3-trifluoropropyl or phenyl, m is an integer from 1 to 50, n is an integer from 2 to 50, o is zero or an integer from 2 to 50, p is an integer from 2 to 4 and r is zero or an integer from 1 to 4 are preferred. Epoxysiloxanes in which $R^3$ to $R^5$ are methyl, m is 2, n is 35, p is 4 and o and r are zero are particularly preferred. The most preferred compounds are reaction products of 4-allyl-2,6-dimethylphenyl, 4-allyl-2,6-di-tert-butylphenyl, 4-allyl-2,6-dicyclohexylphenyl or 4-allyl-2,6-diphenylphenyl glycidyl ether with 1,1,3,3-tetramethyldisiloxane or with a poly-(methylhydrogen)-siloxane having terminal trimethylsilyl groups and having approx 35 methylhydrogen-siloxane units in the chain.

The epoxysiloxanes according to the invention are suitable for use as epoxy resins. They can, for example, be used for the preparation of adhesives, sealing materials, lacquers or encasing resins, and they afford products having excellent properties.

The invention also relates, therefore, to durable epoxy resin compositions of matter comprising (a) an epoxy silane according to the invention and (b) a curing agent and/or a curing catalyst for epoxy resins.

In this regard it is also possible to use mixtures of different epoxy silanes (a) and curing agents (b). The curing component (b) can be either heat-activatable or radiation-activatable.

Suitable epoxy resin curing agents which are radiation-activatable are known. Examples of these are onium compounds, as described, for example, in U.S. Pat. No. 4,069,055, U.S. Pat. No. 4,058,401 and U.S. Pat. No. 4,394,403, or, preferably, metallocene complexes, for example the compounds described in EP-A No. 94,915.

Suitable heat-activatable curing agents (b) are epoxy resin curing agents of any desired type, for example cyanamide, dicyandiamide, polycarboxylic acids, polycarboxylic anhydrides, polyamines, polyaminoamides, adducts formed from amines and polyepoxides, and polyols.

Examples of suitable polycarboxylic acids and anhydrides thereof are phthalic anhydride, tetrahydrophthalic anhydride, hexahydrophthalic anhydride, methyltetrahydrophthalic anhydride, endomethylenetetrahydrophthalic anhydride, hexachloroendomethylenetetrahydrophthalic anhydride, trimellitic anhydride, pyromellitic dianhydride, maleic anhydride, succinic anhydride, nonenylsuccinic anhydride, dodecenylsuccinic anhydride, polysebacic polyanhydride and polyazelaic polyanhydride and the acids belonging to the anhydrides mentioned above.

Aliphatic, cycloaliphatic, aromatic and heterocyclic polyamines, such as ethylenediamine, propane-1,2-diamine, propane-1,3-diamine, N,N-diethylethylenediamine, hexamethylenediamine, diethylenetriamine, triethylenetetramine, tetraethylenepentamine, N-(2-hydroxyethyl)-diethylenetriamine, N-(2-hydroxypropyl)-diethylenetriamine, N-(2-cyanoethyl)-diethylenetriamine 2,2,4-trimethylhexane-1,6-diamine, 2,4,4-trimethylhexane-1,6-diamine, m-xylylenediamine, N,N-dimethylpropane-1,3-diamine, N,N-diethylpropane-1,3-diamine, bis-(4-aminocyclohexyl)-methane, 2,2-bis-(4-aminocyclohexyl)-propane, 2,2-bis-(4-amino-3-methylcyclohexyl)-propane, 3-aminomethyl-3,5,5-trimethylcyclohexlamine (isophoronediamine), m-phenylenediamine, p-phenylenediamine, bis-(4-aminophenyl)-methane, bis-(4-aminophenyl) sulfone, aniline-formaldehyde resins and N-(2-aminoethyl)-piperazine may be mentioned as examples of polyamines which are suitable for use as curing agents. Examples of suitable polyaminoamides are those which are prepared from aliphatic polyamines and dimerized or trimerized, unsaturated fatty acids.

Examples of suitable adducts formed from amines and polyepoxides are adducts formed from aliphatic or cycloaliphatic diamines, such as 1,6-hexamethylenediamine, 2,2,4-trimethylhexane-1,6-diamine, 2,4,4-trimethylhexane-1,6-diamine or isophoronediamine, and known diglycidyl ethers.

Suitable polyol curing agents (b) are, in particular, mononuclear or polynuclear aromatic polyols, including novolaks, such as resorcinol, hydroquinone, 2,6-dihydroxytoluene, pyrogallol, 1,1,3-tris-(hydroxyphenyl)-propane, bis-(4-hydroxyphenyl)-methane, 2,2-bis.(4-hydroxyphenyl)-propane, bis-(4-hydroxyphenyl) sulfone and 4,4'-dihydroxybiphenyl, and also novolaks formed from formaldehyde or acetaldehyde and phenyl, chlorophenol or alkylphenols having up to 9 C atoms in the alkyl moiety, especially kresol novolaks and phenol novolaks.

Preferred curing agents are polycarboxylic anhydrides, such as tetrahydro-, hexahydro- and methyltetrahydro-phthalic anhydride, aromatic polyamines, especially bis-(4-aminophenyl)-methane, bis-(4-aminophenyl) sulfone and m-phenylenediamine or p-phenylenediamine and also dicyandiamide.

The curing agents (b) are employed in the amounts customary in the technology of epoxy resins, advantageously in quantities such that there are about 0.7 to 1.5 equivalents of functional groups of the curing agent (b) to one epoxide equivalent.

It is also possible to use compounds known per se as curing accelerators. The following may be mentioned as examples: complexes of amines, particularly tertiary amines, such as monoethylamine, trimethylamine and octyldimethylamine, with boron trifluoride or boron trichloride, tertiary amines, such as benzyldimethylamine, tris-(dimethylaminomethyl)-phenol, hexamethylenetetramine or 1,6-bis-(dimethylamino)-hexane; urea derivatives, such as N-4-chlorophenyl-N',N'-dimethylurea (monuron), N-3-chloro-4-methylphenyl-N',N'-dimethylurea (chlortoluron), N-(2-hydroxyphenyl)-N'-N'-dimethylurea and N-(2-hydroxy-4-nitrophenyl)-N'-N'-dimethylurea, and substituted or unsubstituted imidazoles such as imidazole, benzimidazole, 1-methylimidazole, 3-methylimidazole, 2-ethyl-4-methylimidazole, 2-vinylimidazole, 2-phenylimidazole, 2-phenyl-4-methylimidazole, 1-(2,6-dichlorobenzoyl)-2-phenylimidazole and 1-(2,4,6-trimethylbenzoyl)-2-phenylimidazole.

Urea derivatives, such as monuron, tertiary amines, especially benzyl dimethylamine, and imidazoles, especially 2-phenylimidazole, 3-methylimidazole and 2-ethyl-4-methylimidazole, are preferred as accelerators.

The invention also relates to curable compositions of matter comprising not only the components (a) and (b), but also (c) further epoxy resins containing no silicon atoms.

Suitable further epoxy resins (c) are, in particular, those having on average more than one group of formula VI

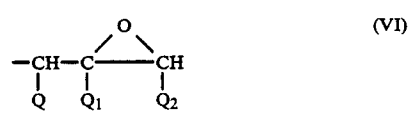
(VI)

attached to a hetero atom, for example to an S atom and preferably to an O or N atom, Q and $Q_2$ in the formula each being a hydrogen atom and $Q_1$ being a hydrogen atom or a methyl group or Q and $Q_2$ together being $-CH_2CH_2-$ or $-CH_2CH_2CH_2-$ and $Q_1$ being a hydrogen atom.

Examples of resins of this type which may be mentioned are polyglycidyl and poly-($\beta$-methylglycidyl) esters derived from aliphatic, cycloaliphatic or aromatic polycarboxylic acids. Examples of suitable polycarboxylic acids are succinic acid, glutaric acid, adipic acid, pimelic acid, suberic acid, azelaic acid, sebacic acid, dimerized or trimerized linoleic acid, tetrahydrophthalic acid, 4-methyltetrahydrophthalic acid, hexahydrophthalic acid, 4-methylhexahydrophthalic acid, phthalic acid, isophthalic acid and terephthalic acid.

Other examples are polyglycidyl and poly-($\beta$-methylglycidyl) ethers which are obtained by reacting a compound containing at least two alcoholic and/or phenolic hydroxyl groups per molecule with epichlorohydrin or with allyl chloride, and subsequently epoxidizing the product with peracids.

Examples of suitable polyols are ethylene glycol, diethylene glycol, poly-(oxyethylene) glycols, propane-1,2-diol, poly-(oxypropylene) glycols, propane-1,3-diol, butane-1,4-diol, poly-(oxytetramethylene) glycols, pentane-1,5-diol, hexane-2,4,6-triol-glycerol, 1,1,1-trimethylolpropane, pentaerythritol and sorbitol; 1,3-cyclohexanediol, 1,4-cyclohexanediol, bis-(4-hydroxycyclohexyl)-methane, 2,2-bis-(4-hydroxycyclohexyl)-propane and 1,1-bis-(hydroxymethyl)-cyclohex-3-ene; N,N-bis-(2-hydroxyethyl)-aniline and 4,4'-bis-(2-hydroxyethylamino)-diphenylmethane; resorcinol, hydroquinone, bis-(4-hydroxyphenyl)-methane (bisphenol F), 2,2-bis-(4-hydroxphenyl)-propane (bisphenol A), 2,2-bis-(4-hydroxy-3,5-dibromophenyl)-propane (tetrabromobisphenol A), 1,1,2,2-tetrakis-(4-hydroxyphenyl)-ethane, 4,4'-dihydroxybiphenyl, bis-(4-hydroxyphenyl) sulfone and novolaks formed from formaldehyde or acetaldehyde and phenol, chlorophenol or alkylphenols having up to 9 C atoms in the alkyl moiety, especially cresol novolaks or phenol novolaks.

Suitable poly-(N-glycidyl) compounds are products obtained by dehydrochlorinating reaction products formed from epichlorohydrin and amines having at least two amine hydrogen atoms. Examples of suitable amines are aniline, n-butylamine, bis-(4-aminophenyl)-methane, 1,3-xylylenediamine, 1,4-xylylenediamine, 1,3-bis-(aminomethyl)-cyclohexane, 1,4-bis-(aminomethyl)-cyclohexane and bis-(4-methylaminophenyl)-methane. Triglycidyl isocyanurate, N,N'-diglycidyl derivatives of cyclic alkyleneureas, such as ethyleneurea and 1,3-propyleneurea, or hydantoins, such as 5,5-dimethylhydantoin, are other suitable compounds of this type.

Examples of poly-(S-glycidyl) compounds are the di-S-glycidyl derivatives of dithiols, such as ethane-1,2-dithiol and bis-(4-mercaptomethylphenyl)ether.

Examples of epoxy resins having one or more groups of the formula VI in which Q and $Q_2$ together are a group $-CH_2CH_2-$ or $-CH_2CH_2CH_2-$ are bis-(2,3-epoxycyclopentyl) ether, 2,3-epoxycyclopentyl glycidyl ether, 1,2-bis-(2,3-epoxycyclopentyloxy)-ethane, 3,4-epoxy-6-methylcyclohexylmethyl-3',4' -epoxy-6'-methylcyclohexane carboxylate and 2-(3,4-epoxy)-cyclohexyl-5,5-spiro(3',4'-epoxy)cyclohexanedioxane.

Epoxy resins which can also be employed are those in which the epoxy groups are attached to hetero atoms of a different kind, or in which one or all of the epoxy groups are located centrally, for example the N,N,O-trigylcidyl derivative of 4-aminophenol, N-glycidyl-N'-(2-glycidyloxyprophy)-5,5-dimethylhydantoin, vinylcyclohexene dioxide, limonene dioxide and dicyclopentadiene dioxide.

It is particularly preferable to employ, as the component (c), diglycidyl ethers, which can be advanced, of dihydric phenols, in particular 2,2-bis-(4-hydroxyphenyl)-propane, 2,2-bis-(3,5-dibromo-4-hydroxyphenyl)-propane, bis-(4-hydroxyphenyl)-methane, bis-(4-hydroxycyclohexyl)-methane or 2,2-bis-(4-hydroxycyclohexyl)-propane, polyglycidyl ethers of novolaks or tetraglycidylated 4,4'-diaminodiphenylmethane. Diglycidyl ethers, which can be advanced, of bisphenol A, tetrabromobisphenol A or bisphenol F, polyglycidyl ethers of phenol/formaldehyde novolaks or cresol/formaldehyde novolaks, or mixtures thereof are very particularly preferred.

If fairly high proportions of epoxy resins (c) are used, for example in proportions of up to 90% by weight, relative to the components (a) and (c), The epoxysiloxanes according to the invention can also act as reactive thinners and as flexibilizers.

The component (b) is employed in the proportions which are usually effective, i.e. adequate for curing the mixtures according to the invention. The ratio of the components (a), (b) and, if appropriate (c) depends on the nature of the compounds used, on the rate of curing required and on the properties desired in the end product, and it can easily be determined by those skilled in the art of curing epoxy resins. If the curing agent (b) is an amine, 0.75 to 1.25 equivalents of amine hydrogen are normally employed per epoxide equivalent. In the case of polycarboxylic acid or polycarboxylic anhydride curing agents, 0.4 to 1.1 equivalents of carboxyl or anhydride groups are generally used per epoxide equivalent. If polyphenols are used as curing agents, it is advantageous to employ 0.75 to 1.25 phenolic hydroxyl groups per epoxide equivalent. Accelerators are generally used in proportions of 0.1 to 5 per cent by weight, relative to the epoxy resins (a) and, if appropriate (c).

If desired, it is possible to add to the curable mixtures, in order to reduce their viscosity, (other) reactive thinners, for example styrene oxide, butyl glycidyl ether, 2,2,4-trimethylpentyl glycidyl ether, phenyl glycidyl ether, cresyl glycidyl ether or glycidyl esters of synthetic, highly branched, mainly tertiary, aliphatic monocarboxylic acids. Other customary additives which the mixtures according to the invention can also contain are plasticizers, extenders, fillers and reinforcing agents, for example coal-tar, bitumen, textile fibres, glass fibres, asbestos fibres, boron fibres, carbon fibres, mineral silicates, mica, powdered quartz, hydrated aluminium oxide, bentonites, kaolin, silica aerogel or metal powders, for example aluminium powder or iron powder, and also pigments and dyes, such as carbon black, oxide colours and titanium dioxide, fire-retarding agents, thixotropic agents, flow control agents, such as silicones, waxes, and stearates, which can also in part be used as mould release agents, adhesion promoters, antioxidants and light stabilizers.

The mixtures according to the invention are used, for example, as adhesives or in surface protection, but are used particularly for the production of cured products for electrical and, in particular, electronic applications. They can be used in a formulation adapted to suit each particular field of use, in an unfilled or filled state, for example as paints, coating compositions, lacquers, compression moulding materials, dipping resins, casting resins, impregnating resins, laminating resins and adhesives. They are particularly suitable for use as adhesives, sealing materials, lacquers or encapsulating resins.

The curing of the mixtures according to the invention can be carried out in a manner known per se in one or two stages. The curing of the mixtures according to the invention is generally effected by heating to temperatures between 80° and 200° C., in particular 100° and 180° C.

Curable mixtures containing radiation-activatable curing agents are suitably cured by means of actinic radiation, as described, for example, in U.S. Pat. No. 4,069,055, U.S. Pat. No.4,058,401, U.S. Pat. No. 4,394,403 or EP-A No. 94,915.

The invention also relates to crosslinked products obtained by curing the curable compositions of matter according to the invention.

The cured products prepared by means of the epoxysiloxanes according to the invention are distinguished by good mechanical, thermal and chemical properties, for example high tensile shear strength, good resistance to heat and resistance to water and also excellent adhesion properties on a variety of substrates.

The invention will be illustrated in greater detail by means of the following examples.

EXAMPLE 1:

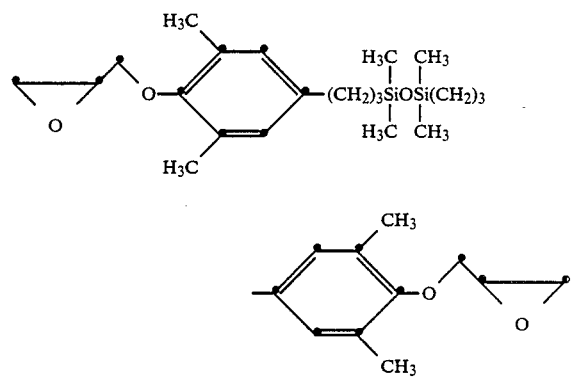

400 g (1.83 mol) of 4-allyl-2,6-dimethylphenyl glycidyl ether (prepared in accordance with Example A of EP-A No. 205,402) and 123.6 g (0.92 mol) of 1,1,3,3-tetramethyldisiloxane (Fluka AG, Buchs, Switzerland) are dissolved in 530 ml of toluene and are heated under reflux for 24 hours in the presence of hexachloroplatinic(IV) acid (18.2 ml of a 0.02 M solution in ethanol). After the solvent has been removed by evaporation, 476.7 g (91%) of a brown epoxysiloxane having a viscosity of 170 mPas (25° C.) and an epoxide content of 3.27 equivalent/kg are obtained.

| Elementary analysis: | % C | % H | % Si |
| --- | --- | --- | --- |
| calculated | 67.32 | 8.83 | 9.84 |
| found | 67.88 | 8.83 | 9.20 |

EXAMPLE 2:

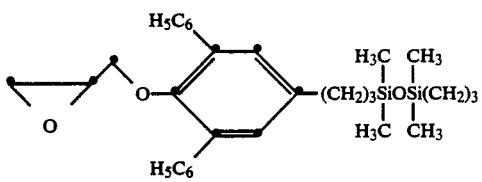

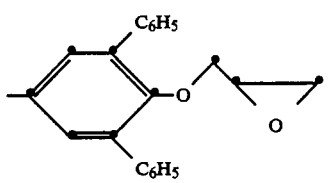

50 g (0.15 mol) of 4-allyl-2,6-diphenylphenyl glycidyl ether (prepared in accordance with EP-A No. 205,402) and 9.8 g (0.075 mol) of 1,1,3,3-tetramethyldisiloxane are dissolved in 100 ml of toluene and are reacted as described in Example 1 in the presence of hexachloroplatinic(IV) acid (1.5 ml of a 0.02 M solution in ethanol). After the solvent has been removed by evaporation, 58.8 g (98%) of an orange-brown epoxysiloxane are obtained.

| Elementary analysis: | % C | % H | % Si |
|---|---|---|---|
| calculated | 76.23 | 7.13 | 6.85 |
| found | 75.80 | 7.00 | 6.30 |

EXAMPLE 3:

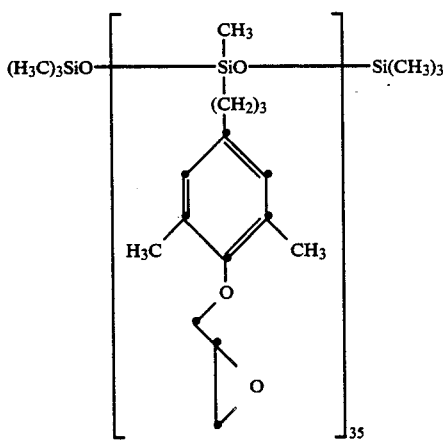

100 g (0.46 mol) of 4-allyl-2,6-dimethylphenyl glycidyl ether and 29.5 g (0.013 mol) of poly-methylhydrogensiloxane of the formula

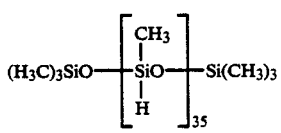

(Fluka AG, Buchs, Switzerland) are dissolved in 200 ml of toluene and are reacted as described in Example 1 in the presence of hexachloroplatinic (IV) acid (4.55 ml of a 0.02 M solution in ethanol). After the solvent has been removed by evaporation, 112 g (86.5%) of a brown epoxysiloxane having a viscosity of 895 mPas (25° C.) or 840 mPas (100° C.) and an epoxide content of 2.91 equivalents/kg are obtained.

| Elementary analysis: | % C | % H | % Si |
|---|---|---|---|
| calculated | 64.38 | 8.09 | 10.49 |
| found | 63.90 | 8.30 | 10.40 |

Use examples:

Example A1

100 parts by weight of the epoxysiloxane according to Example 1 are mixed with 45 parts of hexahydrophthalic anhydride, and the mixture is then cured for 4 hours at 100° C. and for 8 hours at 140° C. The properties of the curable mixture and of the cured product are indicated in Table 1.

Example A2

Example A1 is repeated, employing, as the curing agent, 16 parts by weights of 4,4'-diaminodiphenylmethane instead of hexahydrophthalic anhydride. The properties of the curable mixture and of the cured product can be seen from Table 1.

TABLE 1

| Example | A 1 | A 2 |
|---|---|---|
| Viscosity at 80° C. (mPa.s) | 10 | 20 |
| Gel time at | | |
| 180° C. (min) | 2.00 | 22 |
| 160° C. | 4.83 | 45 |
| 140° C. | 11.50 | 90 |
| Tensile strength, ISO R-527 (N/mm$^2$) | 43 | 36 |
| Elongation, ISO R-527 (%) | 5 | 14 |
| Flexural strength[1], DIN 53,435 (N/mm$^2$) | 74 | 50 |
| Tensile shear strength, ISO 4587 (N/mm$^2$) | 21.7 | 24.5 |
| Water absorption (%) | | |
| 4 days at 23° C. | 0.15 | 0.16 |
| 1 hour at 100° C. | 0.47 | 0.55 |
| Impact resistance[1], DIN 53,435 (kJ/m$^2$) | 13.0 | 41.7 |
| Glass transition temperature, DSC (°C.) | 50 | 57 |
| Loss in weight, thermogravimetric analysis (°C.) | | |
| 5% at | 315 | 290 |
| 10% at | 330 | 310 |

[1]Measured with a 53573 Frank-Dynstat instrument made by Karl Frank GmbH, Weinheim Birkenau, West Germany.

Example A3

The amounts (parts by weight) indicated in Table 2 of epoxy resins, curing agents and accelerators were mixed and cured in each case for 2 hours at 120° C. and for 2 hours at 180° C. The tensile shear strength of the cured systems can be seen in Table 2.

TABLE II

| | 1 | 2 | 3 | 4 | 5 |
|---|---|---|---|---|---|
| Bisphenol A diglycidyl ether (5.25 epoxide equivalents/kg) | 100 | 80 | 60 | 40 | 20 |
| Epoxysiloxane according to Example 1 | 0 | 20 | 40 | 60 | 80 |
| Dicyandiamide curing agent[1] | 10 | 10 | 10 | 5 | 5 |
| Tensile shear strength, ISO 4587 (N/mm$^2$) | 19 | 21 | 23 | 27 | 23.5 |
| 4,4'-Diaminodiphenylmethane curing agent | 25 | 24.6 | 22.4 | 20.5 | 18.8 |
| Tensile shear strength, | 12 | 16 | 17.5 | 21 | 23 |

TABLE II-continued

|  | 1 | 2 | 3 | 4 | 5 |
|---|---|---|---|---|---|
| ISO 4587 (N/mm$^2$) | | | | | |

[1] 0.8% by weight, relative to the total amount of epoxy resins, of N-(4-chlorophenyl)-N',N'-dimethylurea (monuron) is added as accelerator.

The results show that the addition of the epoxysiloxane according to Example 1 substantially increases the tensile strength of the cured systems.

What is claimed is:

1. An epoxysiloxane having, per molecule, at least two groupings of the formula I

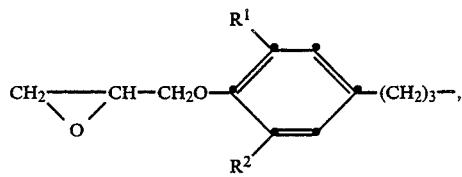

in which R$^1$ and R$^2$ independently of one another are C$_1$-C$_{10}$alkyl, C$_1$-C$_{10}$alkoxy, C$_3$-C$_8$cycloalkyl, C$_6$-C$_{10}$aryl, benzyl or a halogen atom and in which each grouping of the formula I in each case is attached directly to a silicon atom of the siloxane radical.

2. An epoxysiloxane according to claim 1, in which R$^1$ and R$^2$ are identical.

3. An epoxysiloxane according to claim 1, in which R$^1$ and R$^2$ independently of one another are C$_1$-C$_5$alkyl, C$_1$-C$_5$alkoxy, C$_5$-C$_6$cycloalkyl, phenyl, benzyl or a chlorine or bromine atom.

4. An epoxysiloxane according to claim 1, in which R$^1$ and R$^2$ independently of one another are methyl, ethyl, isopropyl, tert-butyl, cyclohexyl, phenyl or a bromine atom.

5. An epoxysiloxane according to claim 1 selected from compounds of the formulae III, IV or V

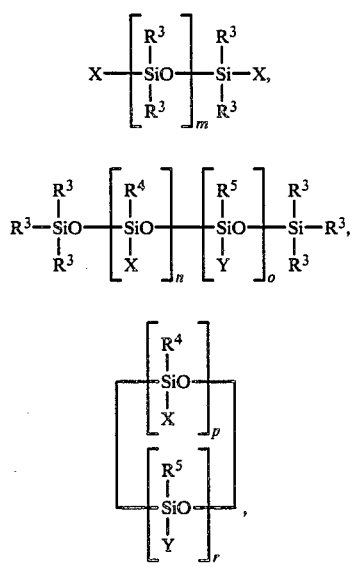

in which R$^3$, R$^4$ and R$^5$ independently of one another are C$_1$-C$_5$alkyl, C$_1$-C$_5$fluoroalkyl or phenyl, X is a grouping of the formula I according to claim 1, Y is one of the radicals R$^3$, R$^4$ and R$^5$ and or a group —(CH$_2$)$_2$—CN or —(CH$_2$)$_2$—COOR$^6$ in which R$^6$ is C$_1$-C$_5$alkyl, m is an integer from 1 to 500, n is an integer from 2 to 500, o is zero or an integer from 1 to 500, p is an integer from 2 to 10, r is zero or an integer from 1 to 8 and p+r is at least 3.

6. An epoxysiloxane according to claim 5, in which R$^3$, R$^4$ R$^5$ and independently of one another are methyl, ethyl, 3,3,3-trifluoropropyl or phenyl, m is an integer from 1 to 50, n is an integer from 2 to 50, o is zero or an integer from 2 to 50, p is an integer from 2 to 4 and r is zero or an integer from 1 to 4.

7. An epoxysiloxane according to claim 6, in which R$^3$ to R$^5$ are methyl, m is 2, n is 35, p is 4, is zero and r is zero.

8. An epoxysiloxane according to claim 1 of the formula

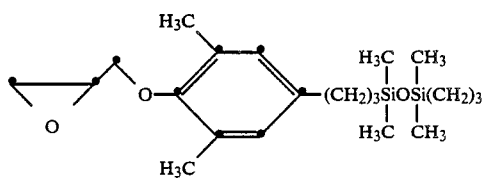

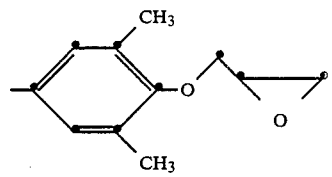

9. An epoxysiloxane according to claim 1 of the formula

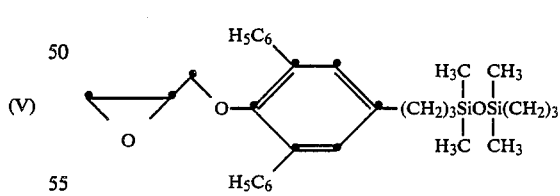

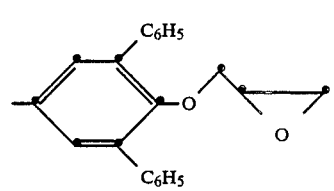

10. An epoxysiloxane according to claim 1 of the formula

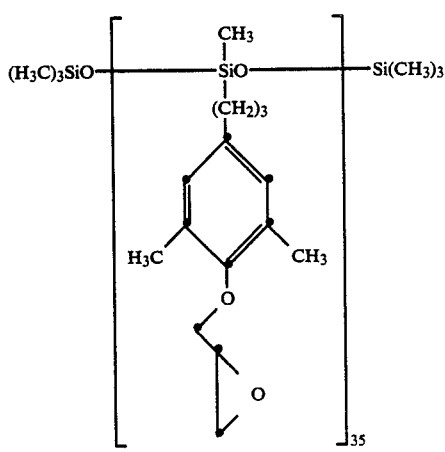

11. A curable epoxy resin composition of matter comprising (a) an epoxysiloxane according to claim 1 and (b) a curing agent and/or a curing catalyst for epoxy resins.

12. A composition of matter according to claim 11 comprising, in addition, (c) an epoxy resin containing no silicon atoms.

13. A composition of matter according to claim 11, in which the component (b) is heat-activatable.

14. A composition of matter according to claim 11, in which the component (b) is radiation-activatable.

15. A crosslinked product obtained by curing the composition of matter according to claim 11.

* * * * *